United States Patent [19]

Goemans

[11] Patent Number: Plant 7,078

[45] Date of Patent: Dec. 19, 1989

[54] ALSTROEMERIA PLANT NAMED APOLLO

[75] Inventor: Frank Goemans, Chichester, England

[73] Assignee: Wuelfinghoff Freesia B.V., Netherlands

[21] Appl. No.: 294,260

[22] Filed: Jan. 6, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Alstroemeria plant named Apollo characterized by its large white flowers, the upper surfaces of the inner petals of which are infused with bright yellow-orange. Brown streaks are present on these upper surfaces, with the streaks increasing in size toward the outer end of the petals.

1 Drawing Sheet

1

The present invention comprises a new and distinct cultivar of Alstroemeria plant known by the cultivar name Apollo.

Apollo was originated by the inventor Frank Goemans from a hybridization made in a controlled breeding program in Chichester, Sussex, United Kingdom in 1984. The female parent was a cultivar designated A49, a hybrid derived from *A. Aurantiaca.* The male parent of Apollo was a cultivar designated S23, a selection from *A. Pulchra.*

Apollo was discovered and selected as one flowering plant within the progeny of the stated parentage by Frank Goemans on June 15, 1984 in a controlled environment in Chichester, United Kingdom.

The first act of asexual reproduction of Apollo was accomplished when vegetative cuttings were taken from the initial selection on June 30, 1984 in a controlled environment in Chichester, United Kingdom by Frank Goemans. Horticultural examination of selected units initiated June 27, 1986 has demonstrated that the combination of characteristics as herein disclosed for Apollo are firmly fixed and retained through generations of asexual reproduction.

Apollo has not been observed under all possible environmental conditions. The phenotype may vary significantly with variations in environment such as temperature, light intensity and day length. The following observations, measurements and comparisons describe plants grown in Spalding Lincs, United Kingdom under greenhouse conditions which approximate those generally used in commercial practice.

The following traits have been repeatedly observed and are determined to be basic characteristics of Apollo which in combination distinguish this Alstroemeria as a new and distinct cultivar:

1. Large white flowers, with upper surface of the inner petals being infused with bright yellow-orange.
2. Streaking appears on the upper surfaces of the inner petals, with the streaks being dark brown and increasing in thickness towards the outer ends of the petals.
3. Long stems.
4. Relatively long flowering season.

Of the many commercial cultivars known to the present inventor, the most similar in comparison to Apollo is Walter Fleming. In comparison to Walter Fleming, Apollo has larger flowers, longer stems, and a longer flowering season.

2

The accompanying photographic drawing shows typical inflorescence and foliage characteristics of Apollo, with colors being as nearly true as possible with illustrations of this type. The photograph is a perspective view of several flowers of Apollo, also showing several buds, and foliage.

In the following description, color references are made to The Royal Horticultural Society Color Chart. The color values were determined in the afternoon of May 21, 1986 under natural light at Spalding, United Kingdom.

Classification:
- *Botanical.*—Alstroemeria cv Apollo.
- *Commercial.*—Alstroemeria.

PLANT

Form: Normal.
Height: A typical plant reaches a tall 65 inches.
Growth: Vigorous.
Foliage:
- *Quantity.*—Medium.
- *Size of leaf.*—7×1.5 inches.
- *Shape of leaf.*—Narrow, obovate.
- *Color.*—Upperside, medium green. Underside, medium green.

Rhizomes:
- *Color.*—White.
- *Size.*—Normal.

INFLORESCENCE

A. Bud
- *Form.*—Normal.
- *Diameter.*—One-half inch.
- *Length.*—One and three-quarters inches.
- *Calyx.*—Elliptic.

B. Flower
- *Size.*—Large, 3½ inches in diameter.
- *Borne.*—Medium number of branches in umbel.
- *Blooming habit.*—Floriferous.
- *Shape.*—Typical.
- *Color*—Upper surface; white infused with 15A and 17A on inner petals; these petals have dark brown streaks which increase in size toward the outer ends of the petals. Under surface; 155D
- *Peduncle.*—Length, 50 inches; Color, medium green
- *Lasting quantity.*—Approximately 10 days

REPRODUCTIVE ORGANS

Stamens: Number, 6.
Anthers: Color, greenish.
Filaments: Color, white.
Pistils: Number, 1; Color, white.

Stigma: Color, white.

I claim:

1. A new and distinct cultivar of Alstroemeria plant named Apollo, as illustrated and described.

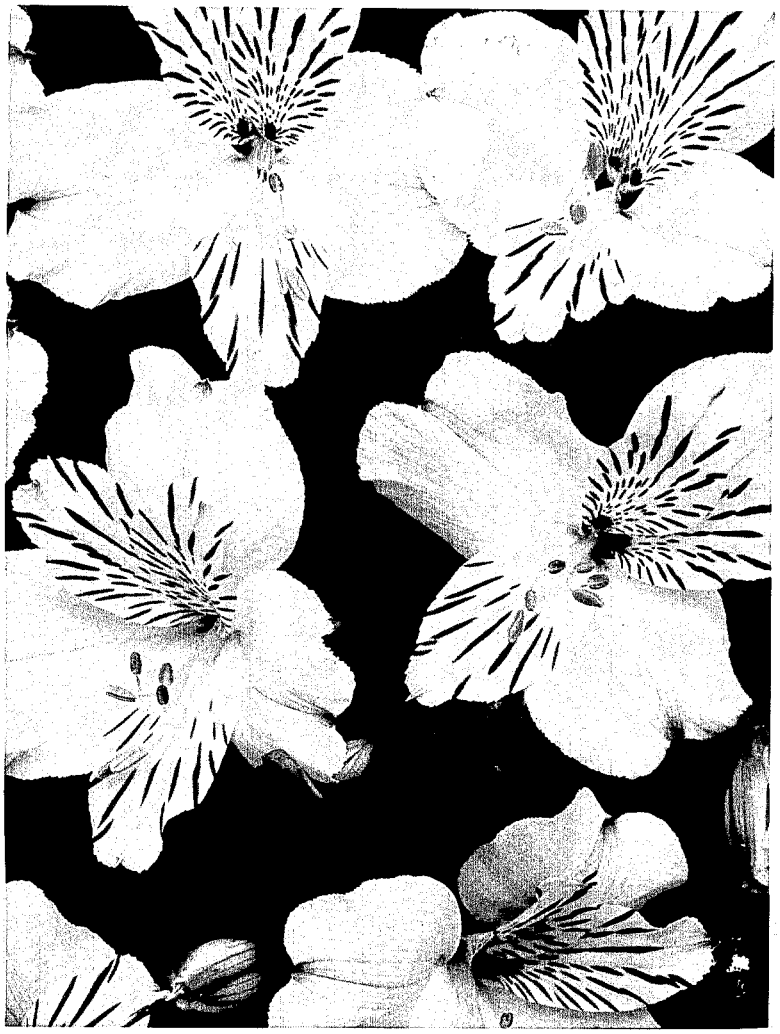

* * * * *